(12) United States Patent
Curiel et al.

(10) Patent No.: US 9,402,695 B2
(45) Date of Patent: Aug. 2, 2016

(54) INDIVIDUALIZED JIG FOR ORTHODONTIC BRACES, ASSEMBLY FORMED BY THAT JIG, A BASE AND A BRACKET, AND ITS DESIGN METHODS

(75) Inventors: Patrick Curiel, Neuilly (FR); William Ayache, Nueilly sur Seine (FR); Philippe Salah, Paris (FR)

(73) Assignee: H32, Paris (FR)

(*) Notice: Subject to any disclaimer, the term of this patent is extended or adjusted under 35 U.S.C. 154(b) by 0 days.

(21) Appl. No.: 13/698,599

(22) PCT Filed: May 17, 2011

(86) PCT No.: PCT/FR2011/051099
§ 371 (c)(1),
(2), (4) Date: Jan. 22, 2013

(87) PCT Pub. No.: WO2011/144857
PCT Pub. Date: Nov. 24, 2011

(65) Prior Publication Data
US 2013/0196279 A1    Aug. 1, 2013

(30) Foreign Application Priority Data
May 17, 2010   (FR) .................................... 10 53777

(51) Int. Cl.
*A61C 7/12* (2006.01)
*A61C 7/14* (2006.01)
(Continued)

(52) U.S. Cl.
CPC .................. *A61C 7/146* (2013.01); *A61C 7/002* (2013.01); *A61C 7/145* (2013.01); *A61C 7/20* (2013.01); *A61C 9/00* (2013.01)

(58) Field of Classification Search
CPC ....................................................... A61C 7/146

USPC .......................................... 433/2, 3, 8–10, 24
See application file for complete search history.

(56) References Cited

U.S. PATENT DOCUMENTS

| 3,738,005 A | 6/1973 | Cohen et al. |
| 4,014,096 A | 3/1977 | Dellinger |

(Continued)

FOREIGN PATENT DOCUMENTS

| DE | 44 07 100 | 9/1995 |
| EP | 0 044 464 | 1/1982 |

(Continued)

OTHER PUBLICATIONS

Merriam-Webster.com. Definition of espouse [retrieved on Oct. 17, 2013]. Retrieved from the Internet: http://www.merriam-webster.com/dictionary/espouse.*

(Continued)

*Primary Examiner* — Ralph Lewis
(74) *Attorney, Agent, or Firm* — Andrus Intellectual Property Law, LLP

(57) ABSTRACT

The invention relates to a customized jig for an orthodontic appliance, to an assembly formed by the jig, a base and a bracket, and to the associated design methods. The customized jig is used to install a bracket-bearing base on a tooth, said base forming part of an orthodontic appliance. The invention is characterized in that: the jig is a cap that covers the tooth, covering the free edge thereof and at least portions of the front and rear surfaces of same; and the shape of the jig is such that it matches that of the base in at least one portion of at least one of the edges thereof. The invention also relates to an assembly formed by a customized base bearing a bracket and a customized jig of the type mentioned above, and to methods for designing one such jig.

10 Claims, 2 Drawing Sheets

(51) Int. Cl.
*A61C 7/00* (2006.01)
*A61C 7/20* (2006.01)
*A61C 9/00* (2006.01)

(56) References Cited

U.S. PATENT DOCUMENTS

| | | | |
|---|---|---|---|
| 4,117,596 A | 10/1978 | Wallshein | |
| 4,183,141 A * | 1/1980 | Dellinger | A61C 7/146 433/24 |
| 4,248,588 A | 2/1981 | Hanson | |
| 4,526,540 A * | 7/1985 | Dellinger | 433/24 |
| 4,657,508 A * | 4/1987 | Dellinger | A61C 7/146 433/24 |
| 5,368,478 A | 11/1994 | Andreiko et al. | |
| 5,533,895 A | 7/1996 | Andreiko et al. | |
| 5,711,666 A | 1/1998 | Hanson | |
| 5,791,896 A | 8/1998 | Ipenburg | |
| 5,857,850 A | 1/1999 | Voudouris | |
| 5,863,198 A | 1/1999 | Doyle | |
| 5,879,158 A | 3/1999 | Doyle et al. | |
| 5,906,486 A | 5/1999 | Hanson | |
| 6,071,119 A | 6/2000 | Christoff et al. | |
| 6,123,544 A | 9/2000 | Cleary | |
| 6,250,918 B1 | 6/2001 | Sachdeva et al. | |
| 6,264,468 B1 | 7/2001 | Takemoto | |
| 6,293,790 B1 | 9/2001 | Hilliard | |
| 6,350,120 B1 | 2/2002 | Sachdeva et al. | |
| 6,471,512 B1 | 10/2002 | Sachdeva et al. | |
| 6,554,613 B1 | 4/2003 | Sachdeva et al. | |
| 6,565,355 B2 * | 5/2003 | Kim et al. | 433/3 |
| 6,607,382 B1 | 8/2003 | Kuo et al. | |
| 6,632,089 B2 | 10/2003 | Rubbert et al. | |
| 6,688,885 B1 | 2/2004 | Sachdeva et al. | |
| 6,702,575 B2 | 3/2004 | Hilliard | |
| 6,736,638 B1 | 5/2004 | Sachdeva et al. | |
| 6,776,614 B2 | 8/2004 | Wiechmann et al. | |
| 6,790,036 B2 | 9/2004 | Graham | |
| 6,846,179 B2 | 1/2005 | Chapouland et al. | |
| 6,905,337 B1 | 6/2005 | Sachdeva | |
| 7,056,115 B2 | 6/2006 | Phan et al. | |
| 7,077,646 B2 | 7/2006 | Hilliard | |
| 7,094,053 B2 | 8/2006 | Andreiko | |
| 7,252,509 B2 | 8/2007 | Sachdeva | |
| 7,275,930 B2 | 10/2007 | Taub et al. | |
| 7,361,018 B2 | 4/2008 | Imgrund et al. | |
| 7,422,430 B2 | 9/2008 | Sachdeva et al. | |
| 7,578,673 B2 | 8/2009 | Wen et al. | |
| 7,590,462 B2 | 9/2009 | Rubbert et al. | |
| 7,600,999 B2 | 10/2009 | Knopp | |
| 7,641,473 B2 | 1/2010 | Sporbert et al. | |
| 7,658,610 B2 | 2/2010 | Knopp | |
| 7,690,917 B2 | 4/2010 | Marshall | |
| 7,695,278 B2 | 4/2010 | Sporbert et al. | |
| 7,740,476 B2 | 6/2010 | Rubbert et al. | |
| 7,811,087 B2 | 10/2010 | Wiechmann et al. | |
| 7,844,429 B2 | 11/2010 | Matov et al. | |
| 7,866,978 B2 | 1/2011 | Taub et al. | |
| 7,905,724 B2 | 3/2011 | Kuo et al. | |
| 7,950,131 B2 | 5/2011 | Hilliard | |
| 8,002,543 B2 | 8/2011 | Kang et al. | |
| 8,057,226 B2 | 11/2011 | Wiechmann et al. | |
| 8,060,236 B2 | 11/2011 | Hilliard | |
| 8,070,485 B2 | 12/2011 | Schwartz et al. | |
| 8,147,243 B2 | 4/2012 | Wiechmann | |
| 8,235,715 B2 | 8/2012 | Kuo | |
| 2003/0152884 A1 | 8/2003 | Wiechmann et al. | |
| 2003/0224310 A1 * | 12/2003 | Andreiko | 433/3 |
| 2004/0029068 A1 | 2/2004 | Sachdeva et al. | |
| 2004/0072120 A1 | 4/2004 | Lauren | |
| 2004/0166459 A1 | 8/2004 | Voudouris | |
| 2004/0175667 A1 | 9/2004 | Abels et al. | |
| 2004/0175669 A1 | 9/2004 | Abels et al. | |
| 2004/0214129 A1 | 10/2004 | Sachdeva et al. | |
| 2004/0219473 A1 | 11/2004 | Cleary et al. | |
| 2007/0031775 A1 | 2/2007 | Andreiko | |
| 2007/0072143 A1 | 3/2007 | Sommer | |
| 2007/0087302 A1 | 4/2007 | Reising et al. | |
| 2007/0111154 A1 | 5/2007 | Sampermans | |
| 2007/0166658 A1 | 7/2007 | Voudouris | |
| 2008/0154644 A1 | 6/2008 | Butscher et al. | |
| 2008/0227050 A1 * | 9/2008 | Marshall | 433/24 |
| 2008/0254403 A1 | 10/2008 | Hilliard | |
| 2009/0136898 A1 | 5/2009 | Kim | |
| 2009/0220920 A1 * | 9/2009 | Primus et al. | 433/226 |
| 2011/0250556 A1 | 10/2011 | Heiser | |
| 2012/0150494 A1 | 6/2012 | Anderson et al. | |

FOREIGN PATENT DOCUMENTS

| | | |
|---|---|---|
| EP | 0 161 831 | 11/1985 |
| EP | 0 696 444 | 2/1996 |
| EP | 1 080 697 | 3/2001 |
| EP | 1 234 549 | 8/2002 |
| EP | 1 287 789 | 3/2003 |
| EP | 1 702 582 | 9/2006 |
| EP | 2 011 583 | 7/2009 |
| FR | 2 922 753 | 5/2009 |
| JP | 2004-121817 | 4/2004 |
| JP | 2006-043121 | 2/2006 |
| WO | 9410935 | 5/1994 |
| WO | 03068099 | 8/2003 |
| WO | 2008044912 | 4/2008 |
| WO | 2009056776 A2 | 5/2009 |
| WO | 2010028276 | 3/2010 |
| WO | 2010103178 | 9/2010 |

OTHER PUBLICATIONS

International Search Report for International Appln. No. PCT/FR2011/051099.

Wiechmann, Dirk et al; Abstract of Customized brackets and archwires for lingual orthodontic treatment; American Journal of Orthodontics and Dentofacial Orthopedics, vol. 124, No. 5, pp. 593-599.

Japanese Office Action dated Mar. 3, 2015 issued in corresponding Japanese Application No. 2013-510660.

* cited by examiner

INDIVIDUALIZED JIG FOR ORTHODONTIC BRACES, ASSEMBLY FORMED BY THAT JIG, A BASE AND A BRACKET, AND ITS DESIGN METHODS

CROSS-REFERENCE TO RELATED APPLICATIONS

This application is the U.S. national stage application of International Application PCT/FR2011/051099, filed May 17, 2011, which international application was published on Nov. 24, 2011, as International Publication WO 2011/144857 in the French language. The International Application claims priority of French Patent Application 1053777, filed May 17 and was patented as FR 2959929 on Jul. 20, 2012.

BACKGROUND

The invention concerns the production of an individualized orthodontic brace for treating a patient intended to be used mainly in the case of a lingual technique, i.e. with the brace disposed on the non-visible posterior face of the teeth.

Such braces conventionally include:
  at least one orthodontic wire, in other words a metal wire exerting on the teeth a force tending to move them from their initial unsatisfactory position, called the "wrong position", to a final satisfactory position, called the "corrected position"; and
  a series of brackets each provided with at least one groove for receiving an orthodontic wire; these brackets are individually fixed to the teeth of the patient in a particular position enabling the orthodontic wire to transfer to the teeth the rotation forces necessary to move them from the wrong position to the corrected position during the treatment.

Usually one or more orthodontic wires are used, with a single series of brackets each including one or more grooves.

Lingual orthodontic techniques, which have the esthetic advantage that the brace is practically invisible from the outside, began to be developed around 1970. However, at the time they relied on entirely manual design and fabrication of the braces and their use was highly complex. This is because an important element in the success of the treatment is the correct positioning of the bracket and its groove on the tooth, especially relative to its rotation center. This is because this position determines the orientation of the forces that are imposed on the corresponding tooth and thus the orientations of the tooth in various directions in space when it is in the final corrected position. This positioning is much more difficult to achieve with the lingual technique than with the labial or vestibular technique in which the brace is disposed on the anterior face of the teeth, because of the marked angulation of the posterior faces of the teeth. This angulation is farther away from the center of rotation of the tooth relative to the bracket than in the case of a labial technique. This means that a slight error in the positioning of the bracket may position the groove incorrectly, thus rendering the brace incapable of providing the required correction of the position of the tooth.

It is therefore particularly important to position the brackets very accurately, especially on the incisors and canines, the shapes of the internal faces of which are more complex and variable than those of the premolars and molars.

This positioning is usually effected by devices commonly referred to by orthodontists as jigs, an example of which is described in the document US-A-2009/0136890. That jig consists of a plastic material block provided on its lower or upper face with a housing the configuration of which is such that the end of a given tooth can be inserted in it. This insertion is possible in an accurate and effective manner for the success of the treatment only if the morphology of each tooth has been individually digitized beforehand from an imprint of the dental arch of the patient and that morphology has been fed digitally into the control software of a block fabrication machine. Thus the block is produced with a cavity in which the end of the tooth can be inserted exactly. The block also includes a hook-shaped support member having three consecutive sections at right angles to each other. A first section passes through the block, sliding in an appropriate orifice. A third section has its end shaped to be inserted into the groove of a bracket so as to hold it when fitting the bracket and to be easily disengaged therefrom once the bracket has been fitted. The second section joins the other two. To fit the bracket, it is placed at the end of the support member, the tooth is capped with the block and traction is exerted on the support member to press the sole of the bracket against the base previously coated with an orthodontic adhesive. When the adhesive has been polymerized, the support member is disengaged from the bracket and the block is removed.

This device has a number of drawbacks, however. The blocks and support members are bulky, which makes them difficult to fit and uncomfortable for the patient. Moreover, the accuracy of the positioning of the brackets is not always sufficient. On the one hand, the block encompasses only the upper part of the tooth, because it cannot cover a large portion of the posterior face in order not to impede the fitting of the bracket. It follows that there may be a relatively large play in positioning the block during the operation. On the other hand, the multi-part structure of the device means that inaccuracies in the design and fabrication of the various components are cumulative.

BRIEF DISCLOSURE

The object of the invention is to propose a new method for designing and fabricating a jig and the resulting jig, free of the drawbacks referred to above and allowing very precise positioning of the bracket with, for the patient, minimum discomfort and, for the practitioner, an ergonomic fitting procedure.

To this end, the invention provides an individualized jig for placing on a tooth a base carrying a bracket intended to form part of an orthodontic brace, characterized in that:
  the jig is a cap that caps said tooth, covering its free edge and at least portions of its anterior and posterior faces; and
  the jig has a shape such that it is able to espouse the base over at least a portion of at least one of its edges.

It may include means for the practitioner to hold it to place it.

It may include means allowing it to be attached to the base that it surrounds before placing them on the tooth and detached therefrom after fixing the base to the tooth.

It may include a housing for the base intended to surround the latter over at least a portion of at least one of its lateral edges and at least a portion of its longitudinal edge intended to be situated as close as possible to the cutting edge of the tooth.

It may include at least one housing or projection intended to correspond to at least one projection or housing on the base.

The invention also provides an assembly formed of an individualized base carrying a bracket intended to be included in an orthodontic brace and a jig intended to position the base accurately on the corresponding tooth, characterized in that the jig is an individualized jig of the above type.

Said base may be intended for a lingual orthodontic brace.

Said base may be intended for a vestibular orthodontic brace.

The invention further provides a method of designing an individualized jig of the above type, characterized in that:
- a model is produced from an impression of the dental arch and the teeth of the patient in the wrong position;
- a hardware or virtual set-up is produced from the model;
- if the set-up is hardware, a computer image of it is produced;
- an assembly formed by a base and a bracket intended to be integrated into an orthodontic brace is designed digitally for each tooth to be treated; and
- a cap intended to cap the tooth extending over at least respective portions of the anterior and posterior faces of the tooth is designed digitally for each tooth to be treated.

A space the contour of which corresponds to the contour of the base previously designed for said tooth may be digitally subtracted from the cap.

The invention further provides a method of designing an individualized jig of the above type, characterized in that:
- a model is produced from an impression of the dental arch and the teeth of the patient in the wrong position;
- a computer image of the model is produced;
- an assembly formed by a base and a bracket intended to be integrated into an orthodontic brace is designed digitally for each tooth to be treated; and
- a cap intended to cap the tooth extending over at least respective portions of the anterior and posterior faces of the tooth is designed digitally for each tooth to be treated.

A space the contour of which corresponds to the contour of the base previously designed for said tooth may be digitally subtracted from the cap.

The invention further provides a method of producing a jig of the above type, characterized in that said jig is designed digitally by any of the foregoing methods.

The invention further provides a method of producing a jig of the above type, characterized in that the whole of the orthodontic brace the bracket of which corresponding to said jig must form part is digitally designed and fabricated, said brace is positioned on a hardware set-up or on an impression of the dental arch with the teeth of the patient in the wrong position, the assembly formed by said brace and said set-up or said impression is digitized, said jig is digitally designed from said digitization, and said jig is produced, for example by laser sintering fast prototyping.

As will have been understood, the invention consists in designing for each tooth an individualized jig that has the following features:
- the jig caps the tooth concerned, covering its free edge and at least portions of its anterior and posterior faces;
- the jig has a shape such that it is able to espouse the base over at least a portion of at least one of its edges, for example a portion of one of its mesio-distal edges (lateral edges), a portion of both its mesio-distal edges or at least a portion of its occlusal (longitudinal) edge close to the free edge of the tooth; this allows precise relative positioning of the jig and the base, to which the bracket has been fixed beforehand or of which it is an integral part;
- in one particular embodiment, it includes means for fixing, for example clipping, the base to the jig, allowing their separation after fitting the base and bracket assembly.

BRIEF DESCRIPTION OF THE DRAWINGS

The invention will be better understood after reading the following description, given with reference to the following appended figures.

Figure 1:
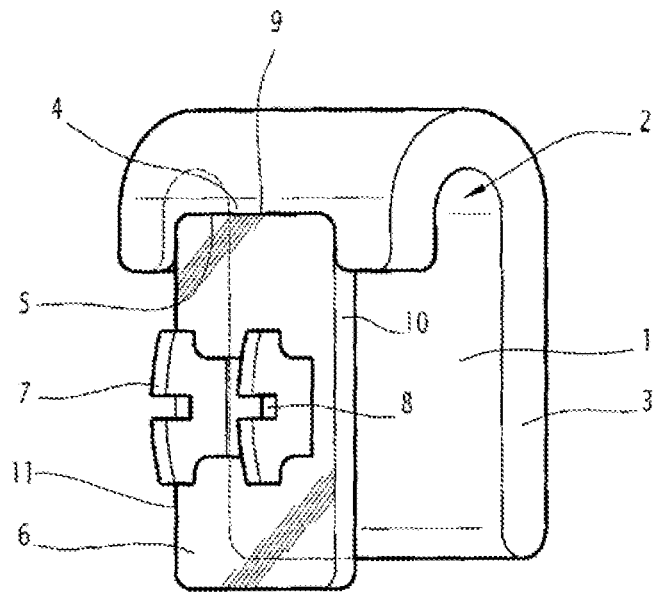
FIG. 1, which shows a first example of the configuration of a jig of the invention and the base that is fixed to it to be positioned on a tooth.

One nonlimiting embodiment of the invention is described next.

DETAILED DISCLOSURE

The first step is to make a plaster model of the dental arch and the teeth of the patient in the wrong position. Then, in a known manner, there is produced what is referred to by orthodontists as the "set-up", i.e. a hardware representation of the dental arch with the teeth in their target corrected positions. To this end the teeth are cut off the foregoing model one by one and placed in their respective target corrected position.

A computer image of this set-up is then produced.

It goes without saying that the set-up can instead be totally virtual, which does not change in any way the principle of the design and use of the jig.

Then, using known methods, for example as described in the document WO-A-03/068099 or WO-A-2009/056776, an assembly formed by a base and a bracket is digitally designed for each tooth. One face of the base espouses the internal face of the tooth and the bracket is fixed to the other face of the base in a chosen position. The following solutions may be adopted in various methods that in the context of the invention are interchangeable:
- the bracket may be a "mass-produced" bracket, i.e. one having a standard shape and standard dimensions, taken from a computer library of brackets when designing the brace; or
- the bracket may be designed and produced "to measure".

An intermediate part may also be provided between the bracket and the base, with a geometry that corresponds to the space which, without it, would be left free at the end of the treatment between the corresponding tooth in its corrected position and the orthodontic wire that passes through the grooves of the brackets during treatment and has returned to its initial shape at the end of treatment (see document WO-A-2009/056776).

In the context of the invention it is immaterial whether the bases, the brackets and any intermediate parts are designed and fabricated separately or are designed and fabricated as individual parts that are joined together. What is essential in the context of the invention is that the digital design of the brace, which includes the configuration of the orthodontic wire (which may be of the so-called "straight wire" type and thus extend substantially in a single plane or extend in three directions in space), leads to a definition of the shape and the dimensions of the assembly including the base and the bracket achieving correct positioning of the groove of the bracket on each tooth so that, through co-operation with the orthodontic wire, each tooth is moved to its corrected position at the end of the treatment, and to a definition of the contours of the base.

The jigs of the invention are then designed in the following manner. A cap is designed that is intended to cap the tooth and extend over at least respective portions of the anterior and posterior faces of the tooth. A space the contour of which corresponds to the contour of the previously designed base is then subtracted digitally from the part of the cap intended to extend over the posterior face of the tooth. The result of this subtraction is the external configuration that must be imparted to the jig so that, after fastening the base and the bracket that it carries to a jig, and after placing the jig in position on the tooth, the base is on the posterior face of the tooth in the exact target position, with great accuracy. The adhesive or any other fastening means with which the base has previously been coated fixes the base to the tooth, after which the jig may be removed.

Alternatively, the edge of the jig that espouses the base may be designed directly, without performing the subtraction just referred to.

The base may be clipped to the jig or fixed by any other means before installing the jig on the tooth. The exact configurations of the base and the jig may be adapted to allow this fixing. This being said, it is not obligatory to fix the base to the jig before installing the jig on the tooth. It is also perfectly feasible to proceed first to installing the jig on the tooth and then to applying the base to the tooth, causing it to butt against the edges of the space provided for this purpose in the jig.

The jig is optimally produced by a fast prototyping laser sintering method with a dimensional accuracy of the order of 20 µm. Other fast prototyping methods may be used, for example plastic prototyping, lost wax prototyping, etc. At present laser sintering offers the greatest accuracy.

Over and above guaranteeing excellent accuracy of the positioning of the base and bracket assembly, the jig of the invention has the advantage over prior art jigs that it is very compact in the mouth. Its walls may be made very thin, less than 1 mm (for example 0.6 mm) thick. Compared to the jigs in the form of blocks of the prior art (see document US-A-2009/0136898), they are much more compact and thus much less uncomfortable for the patient when fitting the orthodontic brace and leave the orthodontist more room for fitting bases to the other teeth without first removing the jigs already fitted.

The various figures show diagrammatically examples of configurations of jigs of the invention.

FIG. 1 shows a jig 1 intended to cap an incisor, not shown, which must be accommodated in the space 2 defined between the anterior part 3 and the posterior part 4 of the jig. It must be understood that the shape of the space 2 as represented in the figures is highly schematic and simplified compared to the real shape that corresponds exactly to that of a tooth. In the example shown, the anterior part 3 covers a relatively large fraction of the anterior face of the tooth. The posterior part 4 of the jig of the invention includes a notch 5 with contours that are adapted so that the base 6 to be fitted to the tooth, which carries a bracket 7 provided with a groove 8 for inserting the orthodontic wire, may be lodged therein, for example clipped therein. As already stated, the configuration of this notch 5 may have been obtained by direct design or by digital extraction during the design of the brace.

In FIG. 1, the notch 5 forms a housing trapping the upper edge 9 and a portion of each lateral edge 10, 11 of the base 6.

Figure 2:
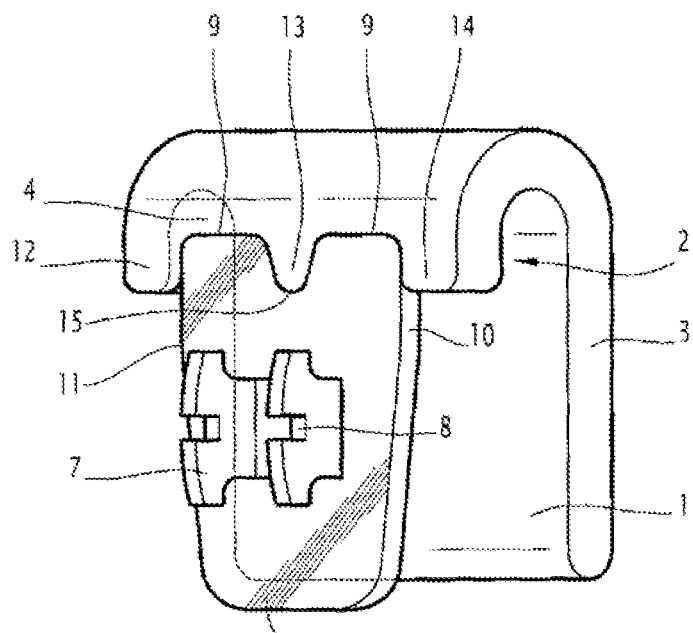
FIG. 2 shows a second exemplary configuration of a jig that includes lateral points and a central point.

In FIG. 2, the posterior face 4 of the jig 1 is in the shape of a trident with points 12, 13, 14 that define a housing for the base 6. The upper edge 9 of the base 6 has a central notch 15 receiving the central point 13 of the trident, the lateral points 12, 14 of the trident framing the lateral edges 10, 11 of the base 6 over a portion of their upper part.

Figure 3:
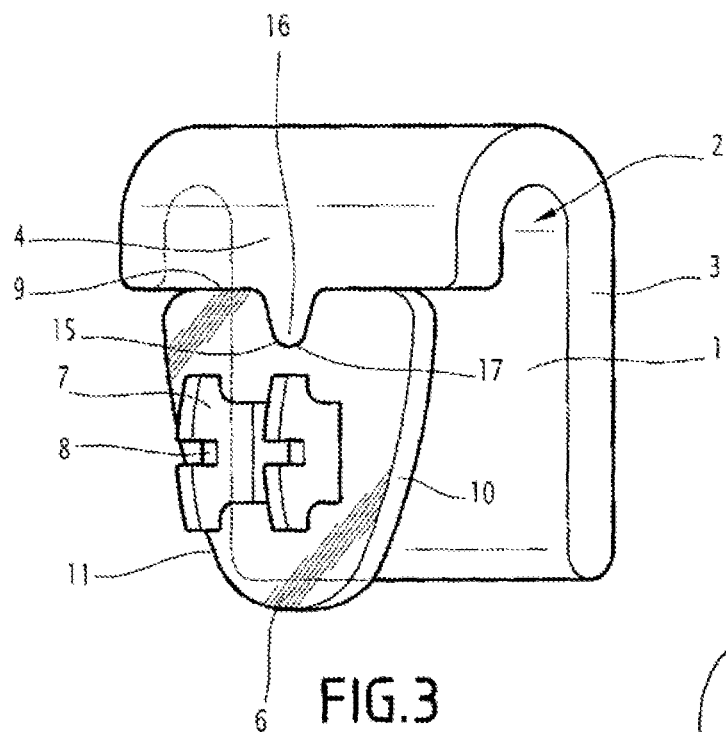
FIG. 3 shows a third exemplary configuration of a jig that includes a central point.

In FIG. 3, the jig 1 is comparable to that from FIG. 2 except that its posterior face 4 includes only one point 16 over which is placed a notch 17 in the upper edge 9 of the base 6. The lateral edges 10, 11 of the base 6 are entirely free of any contact with the jig 1.

Figure 4:
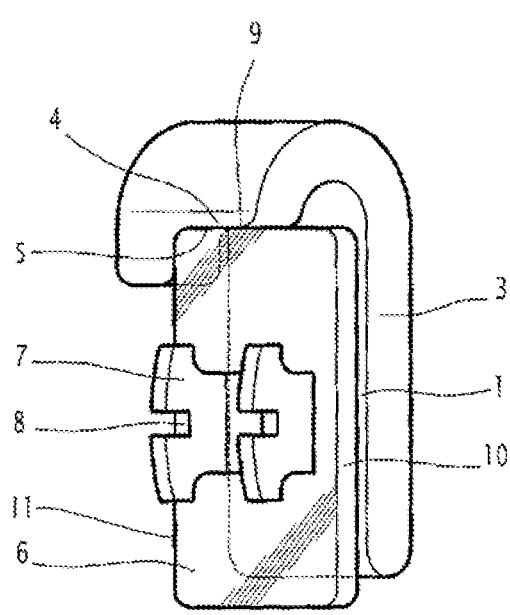
FIG. 4, which shows another configuration of a jig of the invention, which is in fact identical to half of the jig shown in FIG. 1 and is intended to be used on teeth where access is difficult.

In FIG. 4, the jig 1 is identical in principle to that from FIG. 1, except that it is designed to cover only substantially one longitudinal half of the tooth, in other words only one lateral edge 11 and half the upper edge 9 of the base 6 are in contact with the jig. Such a configuration may be advantageously used when the corresponding tooth of the patient, in its wrong position, has a large overlap with an adjacent tooth, leaving insufficient room to fit a jig 1 from FIG. 1. As will be evident to the person skilled in the art, the embodiments of FIGS. 2 and 3 may also be adapted in a similar manner if there is insufficient space for fitting jigs as shown. The jig 1 modified in this way may have a width slightly greater than or slightly less than half the tooth, according to the room available for fitting it or other constraints on the design of the jig.

The description that has been given concerns a jig intended to place a base and its bracket intended to form part of a lingual orthodontic brace. However, the invention could be used in the vestibular technique subject to adaptations that will be evident to the person skilled in the art.

It must be understood that the base 6 may be small, especially in terms of thickness, most importantly for brackets 7 intended for vestibular braces.

Figure 5:
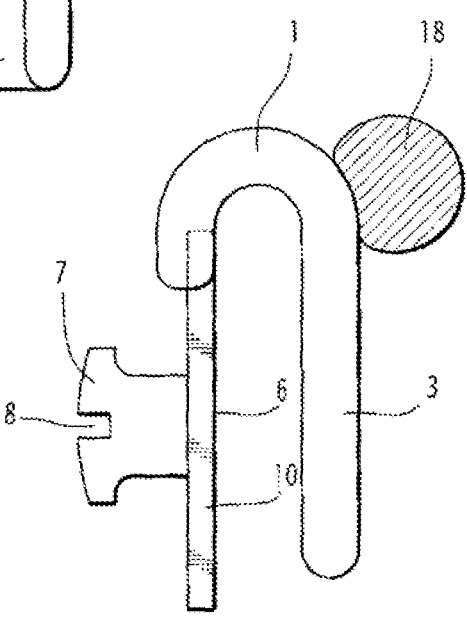
FIG. 5, which shows in profile a variant of the invention in which the jig includes a device facilitating its holding by the practitioner.

In FIG. 5, the jig 1 has on its interior face a ball 18 that serves as a holding member facilitating manipulation of the jig 1 by the surgeon. This holding member may have any shape: ring, rod, cube, etc. or any more complex shape enabling holding of the jig 1 by means of an instrument. It may be placed anywhere on the anterior face (or the posterior face in the case of jigs used in the vestibular technique), at a position in which it will not be in contact with the teeth and/or the adjacent jigs.

Should the practitioner so wish, the completely "made to measure" production of the whole of the jig in all cases allows "first fitting" of the brackets, i.e. fitting during the initial phase of the treatment. In some cases this feature will avoid the practitioner having to defer the fitting of one or more brackets to the teeth that are the most difficult to access. This significantly accelerates treatment.

Alternatively, the design of the jig may be based not on a set-up but on a model of the dental arch with the teeth in the wrong position. This has the advantage of showing up more clearly the spaces available for fitting the jigs and deducing whether or not to give them a particular shape such as that shown in FIG. 4, as well as the best position for the holding member, if any.

Another variant entails designing and fabricating the orthodontic brace (brackets, bases and orthodontic wire) according to the principles described in the document WO-A-2009/056776, for example, positioning on a hardware set-up or on the model of the dental arch with the teeth in the wrong position, then digitizing everything, and then designing the jigs of the invention from the digitized image. The jigs are finally produced by one of the methods described.

The invention claimed is:

1. An orthodontic assembly comprising:
    a bracket comprising a top, a bottom, and a groove through the top configured to receive an archwire therein;
    a base extending outward from the bottom of the bracket, the base having an occlusal edge, a first lateral edge, a second lateral edge, a gingival edge, a first base face contoured to correspond exactly to a tooth to which the base is intended to be secured and a second base face opposite the first face and secured to the bottom of the bracket; and a jig comprising a first part configured to extend along a portion of a first face of the tooth and ending in a first gingival edge, and a second part configured to extend along a portion of a second face of the tooth, the first part and second part define a space therebetween which corresponds exactly to the tooth to which the base is intended to be secured;

wherein the second part comprises a first lateral point extending gingivally, the second part and first lateral point defining a second gingival edge which defines a housing for the base the housing being open in a direction away from the first part and is contoured to correspond exactly to a contour of at least a portion of the occlusal edge and the first lateral edge of the base and the base is fixed to the jig in the housing, wherein the bracket extends exterior the jig and is free from direct engagement with the jig.

2. The orthodontic assembly of claim 1, wherein the second part terminates at the second gingival edge and the first gingival edge of the first part extends gingivally past the second gingival edge of the second part.

3. The orthodontic assembly of claim 1, further comprising a second lateral point extending gingivally, the second the second lateral point further defining the second gingival edge and the housing, wherein the second gingival edge is further contoured to correspond exactly to a contour of at least a portion of the second lateral edge of the base.

4. The orthodontic assembly of claim 3 wherein the base is removably fixed to the jig within the housing.

5. The orthodontic assembly of claim 3 wherein the first lateral edge is a mesial edge and the second lateral edge is a distal edge.

6. The orthodontic assembly of claim 5 wherein the bracket further comprises at least one tie wing at a top of the bracket and the at least one tie wing is free from engagement with the first and second lateral points.

7. The orthodontic assembly of claim 1 further comprising a central point extending from the second part, the central point is contoured to correspond exactly to a notch in the occlusal edge of the base.

8. The orthodontic assembly of claim 1 wherein the first part is configured to extend along an anterior face of the tooth and the second part is configured to extend along a posterior face of the tooth.

9. The orthodontic assembly of claim 1 wherein the bracket further comprises at least one tie wing extending from the top of the bracket at an occlusal edge of the bracket, and wherein the second part does not extend to the at least one tie wing.

10. The orthodontic assembly of claim 1 wherein the base extends outward beyond a perimeter of the bracket in all directions.

* * * * *